United States Patent [19]

Arita et al.

[11] 4,209,376
[45] Jun. 24, 1980

[54] APPARATUS FOR INTEGRATING ELECTROLYTIC CORROSION ASSOCIATED VOLTAGE

[75] Inventors: Yoichi Arita, Toyonaka; Shinko Yada, Katano; Ko Onishi, Nishinomiya, all of Japan

[73] Assignees: Sanyo Electric Co., Ltd.; Osaka Gas Co., Ltd, both of Japan

[21] Appl. No.: 573,789

[22] Filed: May 1, 1975

[30] Foreign Application Priority Data

| May 8, 1974 [JP] | Japan | 49-52663[U] |
| Oct. 7, 1974 [JP] | Japan | 49-115960 |
| Oct. 7, 1974 [JP] | Japan | 49-115961 |

[51] Int. Cl.² ............... G01N 27/46; G01N 27/30
[52] U.S. Cl. ............................................. 204/195 C
[58] Field of Search ........................... 204/1 C, 195 C

[56] References Cited

U.S. PATENT DOCUMENTS

| 2,803,797 | 8/1957 | Cowles | 324/29 |
| 2,943,027 | 6/1960 | Schaschl et al. | 204/1 C |
| 3,753,110 | 8/1973 | Ikeda et al. | 324/18 Z |

OTHER PUBLICATIONS

E. C. Potter, "Electrochemistry", Macmillan, N.Y. (1961), pp. 264-268.
F. A. Champion, "Corrosion Testing Procedures", Second Edition, Wiley, N.Y. (1965), pp. 309-315.
L. L. Shreir, Editor, "Corrosion", Newnes, Ltd., London (1963), pp. 11.45-11.49.
K. G. Compton, "Corrosion", vol. 14, 237t-244t (1958).
H. Uhlig, "Corrosion & Corrosion Control", Second Edition, Wiley, N.Y. (1971), pp. 206-211.

Primary Examiner—Aaron Weisstuch
Attorney, Agent, or Firm—Staas & Halsey

[57] ABSTRACT

An electrolytic corrosion associated voltage integrating apparatus comprising a first terminal to be connected to an electric conductor, such as a gas pipe, water pipe, telephone cable or the like, installed in electrical contact with the earth and a second terminal to be connected to an earthed reference electrode; a solid state electrochemical potential memory device which exhibits a terminal voltage between an anode and a cathode linearly changing as a function of the charging or discharging quantity of electricity fed to the device and which is capable of holding the terminal voltage, said device being connected to the terminals to receive an input therefrom; a reference voltage source for compensating the said conductor-to-earthed reference electrode potential input for a potential difference developed between the said earthed reference electrode and the earth per se; and means for displaying the terminal voltage of the device. A preferred embodiment of the present invention comprises means for adjusting the reference voltage of the said reference voltage source. The value indicated by the said displaying means is qualitatively associated with an amount of electrolytic corrosion occurring in the conductor during the time period when the apparatus is connected to the conductor and the earthed reference electrode.

17 Claims, 13 Drawing Figures

APPARATUS FOR INTEGRATING ELECTROLYTIC CORROSION ASSOCIATED VOLTAGE

BACKGROUND OF THE INVENTION

1. Field of the Invention

The present invention relates to an apparatus for integrating an electrolytic corrosion associated voltage. More specifically, the present invention relates to an apparatus for providing an indication qualitatively associated with an amount of electrolytic corrosion which occurs in an electric conductor installed in contact with the earth.

2. Description of the Prior Art

In almost all electric railways, the electric cars are energized by a DC voltage source. Typically, a DC voltage is supplied between a supply line and a rail in view of the fact that the rail is a good electric conductor. The electric car is thus supplied with the electric power from a supply line and a rail, while the car moves along the rail. The fact that the rail is installed in contact with the earth, however, can cause an undesirable situation. More specifically, as is often the case with a city or town, other electric conductors, such as water pipes, gas pipes, telephone cables, power cables and the like, are installed in the earth, which can extend along and in the vicinity of the rails of the electric railways. Therefore, it can often occur that a portion of the power current of the electric railways flows through the earth and the adjacent other electric conductors by way of leakage. It has been well known that electric conductors, such as rails, pipes, cables or the like, installed in contact with the earth are corroded in an electrolytic manner, as a result of leakage current or corrosion current flowing from the conductor to the earth. Thus, it is most important that those who maintain such electric conductors are aware of tendency of such corrosion occurring in the conductor.

A typical prior art method of providing an indication qualitatively associated with an amount of the corrosion occurring in an electric conductor installed in contact with the earth is as follows. A change in voltage as measured between an electric conductor and an earthed reference electrode installed in ideal, good electric contact with the earth is recorded on a record medium, such as a record sheet. The area of the waveform thus obtained is calculated. It is well known that the above-mentioned conductor-to-earthed reference electrode potential is qualitatively associated with the above-mentioned leakage current and the area of the waveform thus obtained is qualitatively associated with the quantity of electricity carried by the leakage current, which is closely related to the amount of the corrosion. However, such a method is disadvantageous in that it is very tiresome and of low accuracy. Another prior art approach to provide an indication associated with the amount of corrosion comprises utilization of a silver or copper coulometer, in which the amount, and specifically the weight, of silver or copper deposited within the coulometer due to the flow of leakage current caused by the conductor-to-earthed reference electrode potential indicates the leakage current, and thus the amount of corrosion. This approach is also of low accuracy. It is desired to provide an apparatus capable of providing with accuracy and ease an indication of the above-mentioned area of the waveform of the conductor-to-earthed reference electrode potential, which is qualitatively associated with the amount of electrolytic corrosion which occurs in an electric conductor installed in contact with the earth.

A voltage storing device of interest in connection with the present invention is disclosed in U.S. Pat. No. 3,753,110, issued Aug. 14, 1973 to Hironosuke Ikeda et al and assigned to Sanyo Electric Co., Ltd., the same assignee as that of the present invention. As set forth in the referenced patent, Professor Takehiko Takahashi and Assistant Professor Osamu Yamamoto, Technological Department of Nagoya University, announced their study on the electrochemical potential memory device by the use of a solid state electrolyte at the 22nd annual assembly of Japan Chemical Association held on Apr. 5th to 7th, 1979. Briefly stated, this device comprises an Ag electrode as a cathode, an Ag-Te alloy electrode as an anode, and a solid state electrolyte having high ion conductivity, such as $RbAg_4I_5$ sandwiched between both electrodes. When a DC voltage is applied to the device so that the Ag electrode may be negative, a portion of Ag contained in the Ag-Te alloy electrode migrates over to the Ag electrode, resulting in a decreased activity of Ag in the Ag-Te alloy, and thus an increased potential difference between both electrodes. The inventors of this device termed this state of operation as "charging." When the polarity of the applied DC voltage is reversed to that of the former case, Ag migrates back to, and is refilled into, the Ag-Te alloy, resulting in the potential difference decreasing and returning to the initial value eventually. The inventors of this device termed this state of operation as "discharging." Study disclosed by the inventors of this device indicated that the electromotive force generated by the above-mentioned charging or discharging current underwent linear change to some extent with respect to the charging or discharging quantity of electricity (current-time). Thus, this device makes it possible, as an outstanding characteristic, to do write-in and non-destructive read-out operations while preserving a relatively linear relation between the charging or discharging time and terminal voltage, and in addition, it can hold the memory condition for a relatively long period of time. These advantages mean that this device has potential use as an analog memory device. The referenced patent further discloses an improved electrochemical potential memory device. More specifically, FIG. 6 of the referenced patent shows both an improved electrochemical potential memory device for eliminating the IR drop across the resistance of the electrolyte and the overvoltage caused by dissolution or deposition of Ag, which improved device is basically characterized by the provision of an auxiliary cathode that comprises an output terminal for detecting the potential separately from the above-mentioned cathode utilized as the input terminal for the current conduction.

In view of these advantageous characteristics of the above-mentioned memory device, it may be possible to utilize this device as an essential component of an apparatus for obtaining information relative to electrolytic corrosion by measuring the quantity of electricity flowing therethrough as a result of the application thereto of the above-mentioned conductor-to-earthed reference electrode potential which is qualitatively associated with the leakage current flowing from or to an electric conductor installed in contact with the earth. A prior art apparatus of interest for integrating an electrolytic corrosion associated voltage for realizing the above-mentioned possibility has been disclosed in U.S. patent application, Ser. No. 575,998, entitled "APPARATUS FOR MEASURING ELECTROLYTIC CORROSION," now U.S. Pat. No. 4,003,815, and assigned to Sanyo Electric Co., Ltd., the same assignee as the present invention. More specifically, the referenced application discloses an apparatus for integrating an electrolytic corrosion associated voltage, comprising a solid state electrochemical potential memory device connected to an electric conductor installed in electrical contact with the earth, and to an earthed reference electrode, and means for reading out the output voltage of the said potential memory device. The solid state electrochemical potential memory device exhibits a terminal voltage between an anode and a cathode, which voltage is linearly changing as a function of the charging or discharging quantity of electricity fed to the device, the memory device being capable of holding the terminal voltage. The potential memory device is charged or discharged as a function of the current caused by the conductor-to-earthed reference electrode potential to flow through the said potential memory device from or to the said electric conductor, which current is qualitatively associated with corrosion current flowing through the said electric conductor. Therefore, an output of the memory device as charged or discharged in a predetermined period of time is qualitatively associated with the amount of electrolytic corrosion which is caused by the said leakage current. As a result, tendency of such corrosion can be known.

Nevertheless, the measurement with the electrolytic corrosion associated voltage integrating apparatus disclosed in the cited application is of low accuracy in certain applications such as measurement of the corrosion in an electric conductor, the conductor-to-earthed reference electrode potential of which is low. More specifically, even though an earthed reference electrode is installed to be in ideal, good electrical contact with the earth, the installation of such an earthed reference electrode inherently entails the experiencing of a potential difference between the electrode and the earth per se, which potential difference is characteristic of the material of the reference electrode. Therefore, in the case where a corrosion current is rather small and a conductor-to-earthed reference electrode potential is accordingly low in a certain environment of corrosion measurement, the above-mentioned potential difference proper to the reference electrode material becomes dominant as compared with the conductor-to-earthed reference electrode potential of interest, resulting in low accuracy. It is desired to provide an apparatus capable of providing an integrated indication of conductor-to-earthed reference electrode potential with high accuracy and ease in any environment of such corrosion measurement.

SUMMARY OF THE INVENTION

Briefly stated, the present invention comprises an apparatus for integrating an electrolytic corrosion associated voltage, the apparatus comprising a solid state electrochemical potential memory device connected to an electric conductor installed in electrical contact with the earth and to an earthed reference electrode, a reference voltage source for compensating for a potential difference between the earthed reference electrode and the earth per se, which potential difference is characteristic of the material of the earthed reference electrode, and means for reading out the output voltage of the said potential memory device. The solid state electrochemical potential memory device exhibits a terminal voltage between an anode and a cathode linearly changing as a function of the charging or discharging quantity of electricity fed to the device, and is capable of holding the terminal voltage. The potential memory device is charged or discharged as a function of a current caused by the conductor-to-earthed reference electrode potential to flow through the said potential memory device from or to the said electric conductor, which current is qualitatively associated with the corrosion current flowing through the said electric conductor. Therefore, an output of the memory device as charged or discharged in a predetermined period of time is obtained, while influence caused by the said potential difference between the earthed reference electrode and the earth per se is eliminated, which output is qualitatively associated with the amount of electrolytic corrosion which is caused by the said leakage current.

In a preferred embodiment of the present invention, means responsive to the input conductor-to-earthed reference electrode potential for providing only one polarity component of the potential memory device is provided, whereby only a positive or negative going component of the input conductor-to-earthed reference electrode potential is integrated by the memory device, thereby to provide an indication qualitatively associated with an amount of the corrosion, in view of the fact that the positive going component of the leakage current is usually a primary cause of electrolytic corrosion. In another preferred embodiment of the present invention, the said reference voltage source comprises means for adjusting the reference voltage obtainable therefrom, whereby the apparatus is adapted to any type of earthed reference electrode and any type of corrosion occurring in any type of material of the electric conductor. In a further preferred embodiment of the present invention, two sets of the potential memory device are provided, such that one of them is aimed to measure the integrated value of the conductor-to-earthed reference electrode potential by a positive going component thereof, while the other is aimed to measure the integrated value of the conductor-to-earthed reference electrode potential by a negative going component thereof. Separate measurement of the positive and negative going components of the conductor-to-earthed reference electrode potential is of assistance in the consideration of the electrolytic corrosion of the electric conductor.

Therefore, a principal object of the present invention is to provide an improved apparatus for providing an indication qualitatively associated with an amount of electrolytic corrosion which occurs in an electric conductor installed in electric contact with the earth.

An essential aspect of the present invention is to utilize a solid state electrochemical potential memory device which is charged or discharged as a function of a current caused by a potential developed between an electric conductor installed in electric contact with the earth and an earthed reference electrode while the said conductor-to-earthed reference electrode potential is utilized in such a manner as to compensate for a potential developed between the earthed reference electrode and the earth per se, thereby to provide an indication qualitatively associated with an amount of electrolytic corrosion occurring in the said electric conductor.

Another aspect of the present invention is to charge or discharge a solid state electrochemical potential memory device as a function of a current caused, by a potential between an electric conductor installed in electric contact with the earth and an earthed reference electrode, to flow through the said potential memory device from or to the said electric conductor, while the said conductor-to-earthed reference electrode potential is utilized in such a manner as to compensate for a potential difference developed between the earthed reference electrode and the earth per se by means of a reference voltage source which reference voltage is adjustable, whereby versatile measurement of corrosion is possible.

A further aspect of the present invention is to charge or discharge a solid state electrochemical potential memory device as a function of a positive going or negative going component of a potential between an electric conductor installed in electrical contact with the earth and an earthed reference electrode, while the said conductor-to-earthed reference electrode potential is adjusted in such a manner as to compensate for a potential difference between the earthed reference electrode and the earth per se, whereby an indication qualitatively associated with an amount of electrolytic corrosion occurring in the electric conductor is provided in terms of an output voltage of the potential memory device.

These objects and other objects, aspects and features of the present invention will be better understood when taken in conjunction with the following detailed description made with reference to the accompanying drawings.

DESCRIPTION OF THE PREFERRED EMBODIMENTS

As described in the foregoing section of Description of the Prior Art, the present invention utilizes the prior art electrochemical potential memory device including a solid state electrolyte. As described already, this device has a significant characteristic in that the terminal voltage or electromotive force of the device changes in an approximately linear relation to the charging or discharging quantity of electricity flowing therethrough. Accordingly, prior to a detailed description of the present invention, it would be appropriate to give a more detailed description of such an electrochemical potential memory device.

Figure 1:
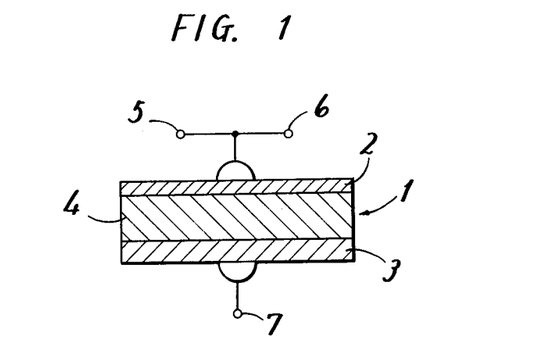
FIG. 1 illustrates a schematic sectional view of an electrochemical potential memory device to be used in the apparatus of the present invention.

FIG. 1 illustrates a schematic sectional view of an electrochemical potential memory device 1 which is used in the apparatus of the present invention. It may be considered that this device is a kind of cell which comprises a solid state electrolyte 4 of high ion conductivity, such as $RbAg_4I_5$ or $Ag_3SI$, sandwiched between a cathode 2 mainly including silver (Ag) and an anode 3 mainly including an alloy of silver and a member selected from the group consisting of sulfur (S), selenium (Se) and tellurium (Te), preferably an Ag-Te alloy. When a DC voltage is applied between electrodes 2 and 3 of this device 1 through an input terminal 5 and a common terminal 7, respectively, in such a way that the anode 3 of this device may be positive and the cathode 2 may be negative, silver contained in the Ag-Te alloy in the anode 3 is ionized and dissolved into the solid state electrolyte 4 and is deposited on the cathode 2. In this specification, such a state of operation is referred to as "charging" hereinafter. When a DC voltage is applied to the above-mentioned device in the directly opposite polarity to the above case, silver deposited over the cathode 2 migrates onto the anode 3 and is deposited thereupon. In this specification, such a state of operation is referred to as "discharging" hereinafter.

Figure 2:
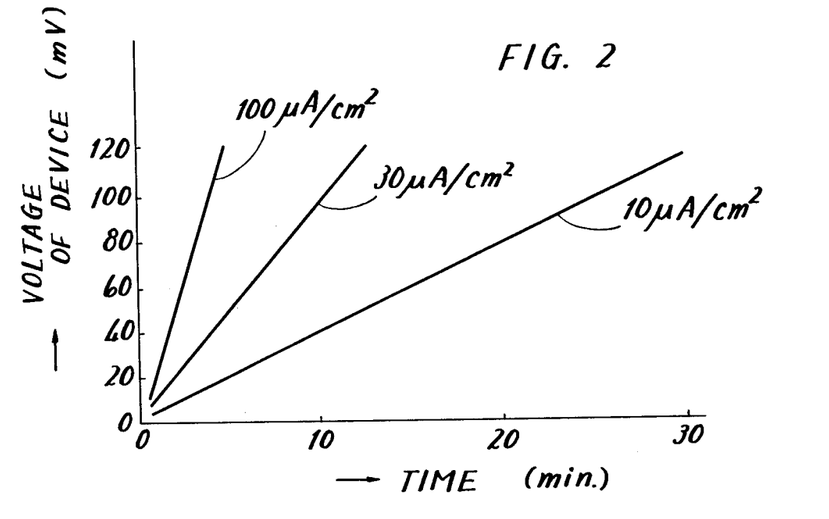
FIG. 2 is a graph which indicates a relation between the charging or discharging time, thus the quantity of electricity, and the electromotive force of the FIG. 1 device, by taking the current for charging or discharging the device as a parameter.

FIG. 2 is a graph which indicates the relation between the charging or discharging time, and thus the quantity of electricity, and the electromotive force of the above-mentioned device, as detected between the electrodes 2 and 3 through an output terminal 6 and the common terminal 7, respectively, by taking the current for charging or discharging the device as a parameter. FIG. 2 illustrates the following functions and characteristics of such a device; the value of the electromotive force of this device as a cell is dependent upon the activity of silver contained in the Ag-Te alloy of cathode 3, the activity of the silver varies rather substantially in response to any slight charging or discharging operation, or current flow when the atomic composition ratio of silver and tellurium contained in the Ag-Te alloy approximates to a value of 2, and the relation between the above-mentioned electromotive force and the charging or discharging quantity of electricity i·t, where i is a current value and t is time, generally is linear during the charging or discharging period where the electromotive force is of a relatively low voltage range (from 0 (zero) to 100 mV. as per the embodiment illustrated in FIG. 2) and also where the current density is of a relatively low order (less than 100 $\mu A/cm^2$ as per the embodiment illustrated in FIG. 2). In this connection, it is to be pointed out that the application of a given voltage to the device in either a charging or discharging manner causes a substantially constant current to flow therethrough and therefore the said linear relation also is demonstrated between the terminal voltage of the device and the charging or discharging time.

It has further been known that this device has an additional characteristic of being capable of holding the potential as established immediately before cutting off the current, even after the cutting off of the current supplied to this device for the above-mentioned voltage range (from 0 (zero) to 100 mV. as per the embodiment illustrated in FIG. 2).

Accordingly, the present invention is directed to providing an apparatus for providing an indication qualitatively associated with an amount of electrolytic corrosion which occurs in an electric conductor installed in electrical contact with the earth, in which such an indication is determined in terms of the output voltage of the potential memory device produced in response to a current supplied thereto and associated with the leakage current which occurs in such an electric conductor.

It is understood that the embodiment described with reference to FIG. 1 includes terminals 5 and 6 connected in common to a single cathode 2 by means of which the charging or discharging current is supplied and also the terminal voltage of the device is detected. In this connection, it is recalled that the device shown in FIG. 1 can be considered as a cell, as mentioned previously. Therefore, in the case of such a device having a common cathode for supply of the current and for detection of the terminal voltage, the detected output voltage is a sum of an electromotive force of the device and of an overvoltage of the device as a cell. This results from the fact that the start or the stop of the electric current conduction into the device causes an overvoltage to be superimposed on the detected voltage and therefore the output voltages detected at the device 1 immediately before and after the change of electrical current conduction state are different. This means that the voltage holding characteristic of the device is degraded. It has been found that the said degradation of the voltage holding characteristic is aggravated by the fact that an increased current for charging and discharging the device causes a greater overvoltage, resulting in more inaccurate measurement. Thus, it is desired to provide an improved potential memory device that eliminates the above-mentioned problem.

The overvoltage as occurs in the electrochemical potential memory device causing a voltage drop after the cutting off of the current conduction into the device may be classified as follows:

(1) A voltage drop caused by the current flowing through the resistance involved in the solid state electrolyte of the device (or an IR drop across the resistance in the electrolyte).

(2) An overvoltage caused by dissolution or deposition of Ag at an interface between the electrolyte and the anode or cathode.

(3) An overvoltage caused by diffusion of Ag ion into the anode.

Figure 3:
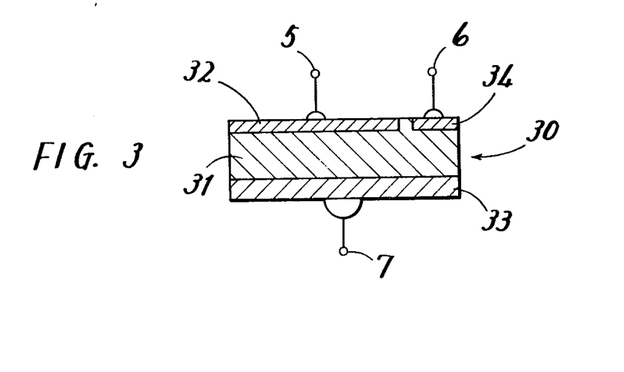
FIG. 3 shows a schematic sectional view of an improved electrochemical potential memory device for eliminating the IR drop across the resistance in the electrolyte and the overvoltage caused by dissolution or deposition of Ag.

FIG. 3 shows a schematic sectional view of an improved electrochemical potential memory device 30 for eliminating the IR drop across the resistance in the electrolyte as described in the above subsection (1) and the overvoltage caused by dissolution or deposition of Ag as described in the above subsection (2). The device 30 shown in FIG. 3 is basically characterized by the provision of an auxiliary cathode 34 that comprises an output terminal 6 for detecting the potential separately from the above-mentioned cathode 32 available for the input terminal 5 for the current conduction. More specifically, the device shown in FIG. 3 essentially comprises a solid state electrolyte 31 composed of $Ag_3SI$, an anode 33 composed of an Ag-Te alloy, a cathode 32 composed of Ag, and an auxiliary cathode 34 composed also of Ag.

Figure 4:
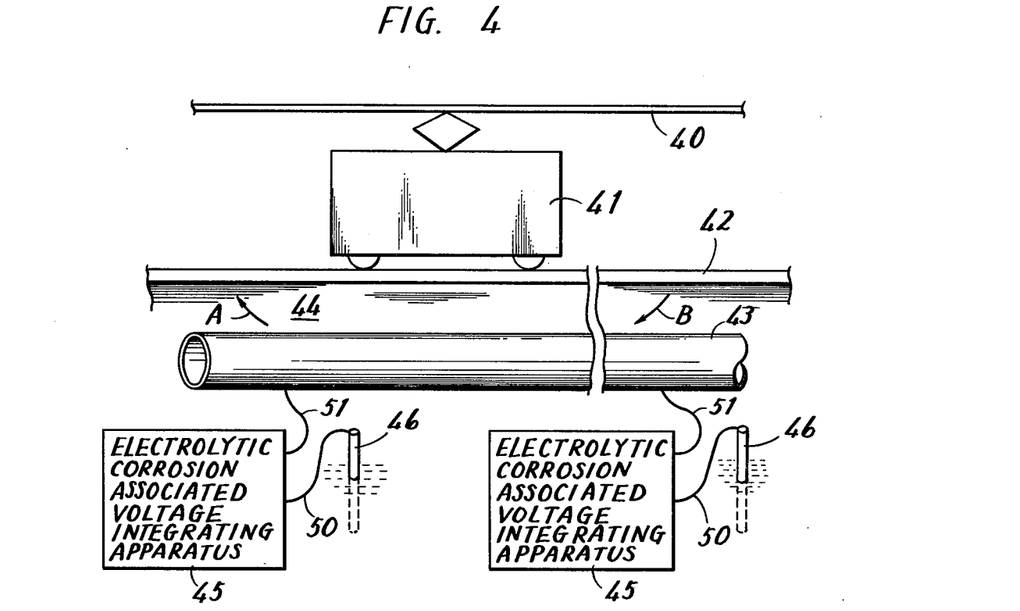
FIG. 4 shows an example of the environments in which the present invention is advantageously utilized.

FIG. 4 shows an example of the environments in which the present invention is advantageously utilized. More specifically, the inventive electrolytic corrosion associated voltage integrating apparatus 45 is shown providing an indication qualitatively associated with an amount of electrolytic corrosion occurring in an electric conductor 43, such as a gas pipe, installed in electrical contact with the earth 44 and extending along and in the vicinity of a rail 42 of the electric railways for an electric car 41 which is supplied with an electric power from a supply line 40. A terminal 51 of the inventive apparatus 45 is connected to the conductor 43 and a terminal 50 of the apparatus 45 is connected to an earthed reference electrode 46 installed in good contact with the earth 44. While the car moves along the rail 42, a corrosion current might flow from the gas pipe 43 toward the rail 42, as shown as an arrow A, in a certain area and a corrosion current might flow from the rail 42 toward the gas pipe 43, as shown as an arrow B, in another area, with the result that in the former area a portion of the gas pipe 43 is corroded in an electrolytic manner while in the latter area a portion of the rail 42 is corroded in an electrolytic manner.

As described in the foregoing section of Description of the Prior Art, the earthed reference electrode 46 inherently entails a potential difference between the reference electrode 46 and the earth 44 per se which potential difference is characteristic of the material of the electrode 46. For example, an earthed reference electrode made of saturated cupric sulfate experiences a potential difference of +850 mV, and an earthed reference electrode made of zinc experiences a potential difference of −260 mV. On the other hand, the conductor-to-earthed reference electrode potential can be as small as the order of 500 mV in a certain environment of corrosion measurement, such as in the case of a gas pipe installed rather remotely from the electric railways. In such a situation, therefore, such a relatively small difference between the conductor-to-reference electrode potential difference and the earthed reference electrode-to-earth potential difference can be a significant cause of error in corrosion measurement. Thus, it is desired to eliminate the influence, if any, on corrosion measurement, of such a potential difference inherently developed between the reference electrode and the earth per se.

Figure 5:
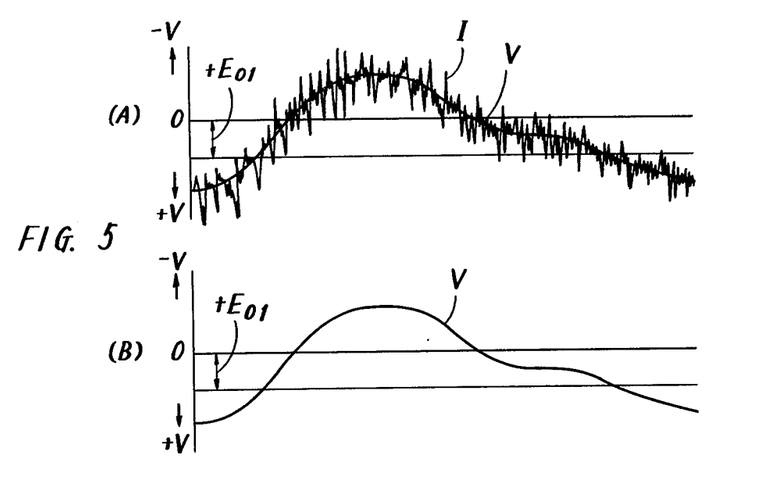
FIG. 5 illustrates a waveform of the conductor-to-earthed reference electrode potential as measured between the gas pipe 43 and the earthed reference electrode 46 which is made of saturated cupric sulfate.

FIG. 5 illustrates a waveform of the conductor-to-reference electrode potential as measured between the gas pipe 43 and the earthed reference electrode 46 which is made of saturated cupric sulfate. In FIG. 5, graph (A) shows a waveform of a composite signal comprising a component designated as V of a relatively low frequency and associated with a corrosion current, and a component as designated as I of a relatively high frequency superimposed on the above-mentioned corrosion current component which is caused as a result of induction of transmission signals of railway communication equipment, while graph (B) shows a waveform of only the corrosion current associated component V as a result of removal of the induced component I by means of a filter circuit to be included in the inventive electrolytic corrosion associated voltage integrating apparatus 45 as to be more fully described hereinafter. In FIG. 5, $+E_{01}$ indicates the above-mentioned earthed reference electrode-to-earth potential difference of $+850$ mV which is characteristic of the earthed reference electrode material of saturated cupric sulfate.

Figure 6:
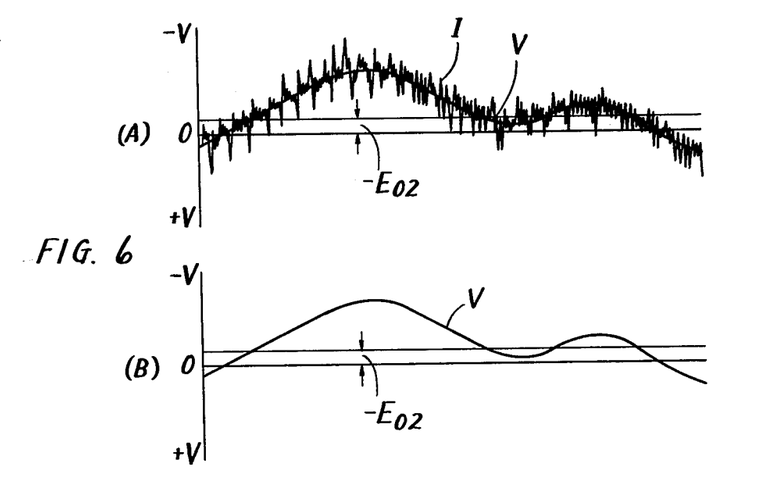
FIG. 6 is a graph similar to that of FIG. 5 but illustrates a waveform as measured with an earthed reference electrode made of zinc.

FIG. 6 is a graph similar to that of FIG. 5 but illustrates a waveform as measured with an earthed reference electrode made of zinc. Therefore, it should be pointed out that in FIG. 6 $-E_{02}$ shows an earth electrode-to-earth potential difference of $-260$ mV which is characteristic of the earthed reference electrode material of zinc.

Figure 7:
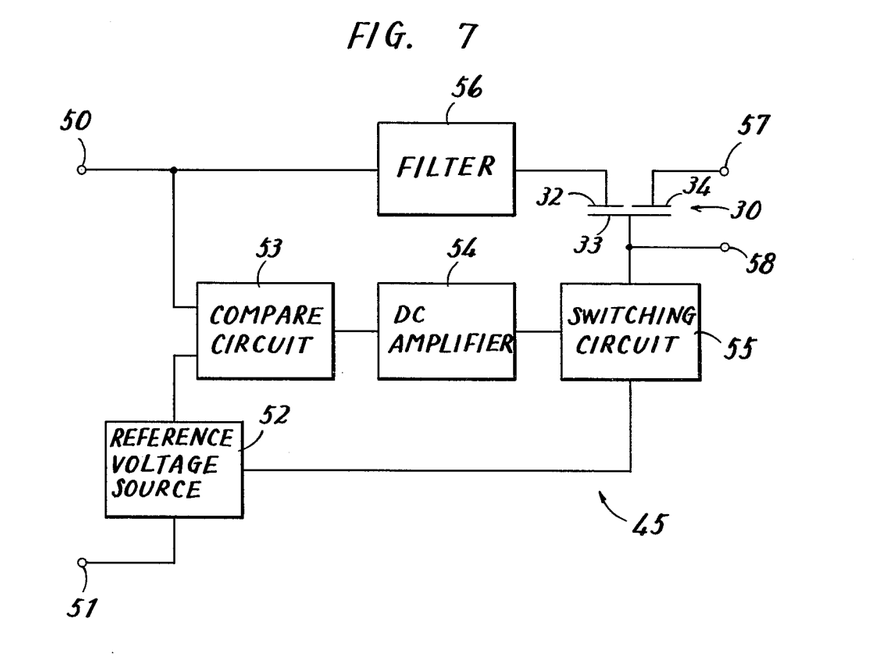
FIG. 7 illustrates a block diagram of an embodiment of the inventive apparatus 45 for integrating an electrolytic corrosion associated voltage.

FIG. 7 illustrates a block diagram of an embodiment of the inventive electrolytic corrosion associated voltage integrating apparatus 45. An input signal obtainable at the terminal 50 from the earthed reference electrode 46 is fed to one input of a comparison circuit 53 and is also fed through a filter circuit 56 to a main cathode 32 of an electrochemical potential memory device 30. The terminal 51 connected to the conductor 43 is connected through a reference voltage source 52 to the other input of the compare circuit 53, and also to the switching circuit 55 (to provide proper biasing of switching circuit 55, as explained in detail below relative to FIG. 8) which is connected to the anode 33 of the potential memory device 30. According to the present invention, it is extremely important that the reference voltage source 52 be adapted to provide a reference voltage to the above-mentioned other input of the comparison circuit 53 in order to compensate for the above-mentioned earthed reference electrode-to-earth potential difference which is characteristic of the material of the earthed reference electrode 46. An output from the comparison circuit 53 is fed to a DC amplifier 54 where the comparison output is amplified and fed to the above-mentioned switching circuit 55 to control the conduction through the potential memory device 30. An output from the potential memory device 30 is obtained between auxiliary cathode 34 and the anode 33 as is measured across output terminals 57 and 58.

In operation, a conductor-to-reference electrode potential as shown as graph (A) in FIGS. 5 and 6 as measured between the gas pipe 43 and the earth electrode 46 is supplied through the terminals 51 and 50 to the inventive electrolytic corrosion associated voltage integrating apparatus 45 in which the input potential signal is supplied to the comparison circuit 53 with the intervention of the reference voltage source 52. As a result, the comparison circuit 53 performs a comparison operation of the conductor-to-reference electrode potential as measured between the gas pipe 43 and the earthed reference electrode 46 under the biasing influence of the reference voltage obtainable from the reference voltage source 52, so as to provide an output therefrom only if and when the conductor-to-reference electrode potential exceeds the reference voltage, that is, when the true conductor-to-earth potential difference is greater than zero. Thus, compensation for the influence of the reference electrode-to-earth potential difference on the accuracy of the corrosion measurement is provided. The output from the comparison circuit 53 is amplified by the DC amplifier 54 and is fed to the switching circuit 55 to turn the circuit 55 on, thereby allowing the potential memory device 30 to be charged by a current with the induced transmission signals filtered out by means of the filter circuit 56. As a result, the potential memory device 30 is charged with the current caused to flow by the conductor-to-earthed reference electrode potential, while any influence caused by the earthed reference electrode-to-earth potential difference characteristic of the material of the earth electrode is eliminated. Thus, it is seen that the apparatus of the embodiment shown in FIG. 7 always provides at the output terminals 57 and 58 an integrated value of the above-mentioned conductor-to-earth potential. It has been observed that such an integrated value of the conductor-to-earth potential is qualitatively associated with an amount of electrolytic corrosion occurring in an electric conductor such as the gas pipe 43 installed in contact with the earth due to the leakage current flowing therefrom. Thus, the present invention makes it possible to provide an indication qualitatively associated with an amount of such electrolytic corrosion of an electric conductor with extreme ease and without any influence by the earthed reference electrode-to-earth potential difference characteristic of the earthed reference electrode material. If an earthed reference electrode made of saturated cupric sulfate is employed, the reference voltage source 52 is adapted to provide a reference voltage which compensates for the above-mentioned potential difference $+850$ mV which is characteristic of the electrode material of saturated cupric sulfate, and if an earth electrode made of zinc is employed, the reference voltage source 52 is adapted to provide a reference voltage which compensates for the above-mentioned potential difference of $-260$ mV which is characteristic of the reference electrode material of zinc.

Figure 8:
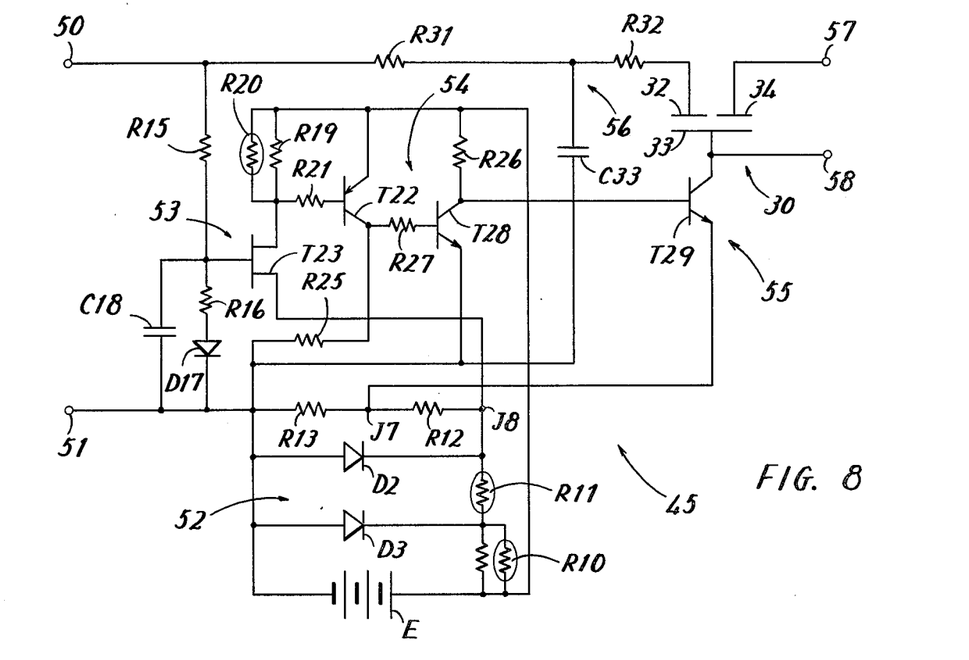
FIG. 8 shows a schematic diagram of an embodiment of the inventive electrolytic corrosion associated voltage integrating apparatus which is particularly adapted to an earthed reference electrode made of saturated cupric sulfate.

FIG. 8 shows a schematic diagram of an embodiment of the inventive electrolytic corrosion associated voltage integrating apparatus which is particularly adapted to an earthed reference electrode made of saturated cupric sulfate. The FIG. 8 embodiment has adopted the basic concept of the FIG. 7 embodiment. Therefore, like portions are designated by the same reference characters. Referring to FIG. 8, the compare circuit 53 comprises a field effect transistor T23, a gate electrode of which is connected to the junction of a resistor R15 and a parallel connection comprising a capacitor C18, a resistor R16 and a diode 17, connected between the input terminals 50 and 51. The reference voltage source 52 comprises a battery E of a relatively constant voltage characteristic such as a nickel cadmium cell which can be advantageously used in the field where the commercial voltage source is not available. In addition, Zener diodes D2 and D3 are connected in parallel with the battery E through thermistors R11 and R10 for the purpose of stabilization of the reference voltage against fluctuation of the voltage caused by variation of voltage of the battery per se and caused by variation of the ambient temperature. The Zener diode D2 is further shunted by a series connection of resistors R12 and R13. The negative electrode of the battery E is connected to the input terminal 51 and the positive electrode of the battery E is connected through a parallel connection of a resistor R19 and a thermistor R20 to the drain of the field effect transistor T23, while a junction J8 of the series connection of resistors R12 and R13 and a series connection of thermistors R11 and R10 is connected to the source of the field effect transistor T23. The DC amplifier 54 comprises transistors T22 and T28. More specifically, the drain of the field effect transistor T23 is connected through a resistor R21 to the base electrode of the transistor T22, an emitter of which is connected to the positive electrode of the battery E and a collector of which is connected through a resistor R25 to the input terminal 51. The collector of the transistor T22 is connected through a resistor R27 to a base of the transistor T28, an emitter of which is connected to the input terminal 51 and a collector of which is connected through a resistor R26 to the positive electrode of the battery E. The filter circuit 56 is implemented by resistors R31 and R32 connected between the input terminal 50 and the main cathode 32 of the device 30 and a capacitor C33 connected between the junction of the resistors R31 and R32 and the input terminal 51. The switching circuit 55 comprises a transistor T29 connected in series with the device 30 between the anode 33 of the device and the junction J7 of the resistors R13 and R12. The base of the transistor T29 is connected to the collector of the transistor T28.

As described previously, the FIG. 8 embodiment has been adapted to compensate for the potential difference characteristic of the earthed reference electrode made of saturated cupric sulfate. Referring to FIG. 5 therefore, it is understood that the potential difference $+E_{01}$ of $+850$ mV should be compensated for. Since the conductor potential input signal is applied through the input terminals 50 and 51 to the gate electrode of the field effect transistor T23 as a result of voltage division by means of the resistor R15 and the resistor R16 and the diode D17, this gate electrode must be biased in a negative direction by the value corresponding to the said potential difference. For this purpose the source electrode of the field effect transistor T23 is connected to the junction J8 between the resistors R13 and R12, on the one side, and the thermistors R11 and R10, on the other side, connected across the battery E to provide the corresponding positive bias to the source electrode of the transistor T23. On the other hand, the emitter of the switching transistor T29 is connected to the junction J7 between the resistor R13 and the resistor R12 so as to provide the corresponding positive bias to the emitter of the transistor T29 as to be more fully described subsequently.

In operation, the conductor-to-reference electrode potential obtainable as between the input terminals 51 and 50 is voltage divided by means of the resistors R15, R16 and diode D17 while induced transmission signals are filtered out by means of the capacitor C18, and is applied to the gate electrode of the field effect transistor T23. Assuming that the input signal at the input terminal 50 is positive (or the input signal at the input terminal 51 is negative) with respect to the predetermined voltage $+E_{01}$ (i.e., the input conductor-to-earthed reference electrode potential is a negative going component), the drain current of the field effect transistor T23 accordingly increases. An increase in the drain current increases a voltage across the parallel connection of the resistor R19 and the thermistor R20 which provides through the resistor R21 an increased bias voltage in a forward direction between the base and the emitter of the transistor T22, so that the base current increases and accordingly the collector current increases. Accordingly, the voltage across the resistor R25 is increased, which provides through the resistor R27 an increased forward bias between the base and the emitter of the transistor T28, so that the base current of the transistor T28 is increased and accordingly the collector current thereof is also increased. An increase in the collector current of the transistor T28 entails a lowered collector voltage thereof, which decreases the base current of the transistor T29 flowing through the resistor R26, so that the transistor T29 is turned off, with the result that any current caused to flow by the conductor-to-reference electrode potential is prevented from flowing through the potential memory device 30. On the other hand, if the input signal at the input terminal 50 is negative (or the input signal at the input terminal 51 is positive) with respect to the predetermined potential difference $+E_{01}$ (i.e., the input conductor-to-reference electrode potential is a positive going component), the above-mentioned operation is reversed and accordingly the switching transistor T29 becomes conductive in the saturated region, so that a current is allowed to flow through the potential memory device 30 from the anode 33 to the main cathode 32, which current corresponds to the difference between the conductor-to-earthed reference electrode potential and the reference voltage, whereby the potential memory device 30 is charged in terms of the present application. It is to be pointed out that the transistors T22 and T28 for implementing the DC amplifier 54 also serve to allow abrupt control of the conduction of the switching transistor T29. Therefore, the number of stages of the transistors T22 and T28 may be increased or decreased in accordance with the desired accuracy. The values of the resistors R31 and R32, as well as that of R13, determine the value of the current flowing through the potential memory device 30. Since the resistors R31 and R32 and the capacitor C33 form the filter circuit 56, the reactance of the capacitor C33 is selected to be smaller than the resistance of the resistor R32 so as to bypass the induced transmission signals.

After measurement of corrosion for a certain period of time by the use of the inventive electrolytic corrosion associated voltage integrating apparatus 45, a terminal voltage between the output terminals 57 and 58 is withdrawn to provide a visual indication of the voltage by the use of a voltage meter (not shown) or to utilize the obtained value in some utilization means. Since the output voltage of the potential memory device 30 shows an accumulated or integrated value of the conductor-to-earthed reference electrode potential minus the earthed reference electrode-to-earth potential, an indication qualitatively associated with electrolytic corrosion occurring in an electric conductor installed in contact with the earth can be provided while influence caused by the earthed reference electrode-to-earth potential difference proper to the earthed reference electrode material is eliminated.

Figure 9:
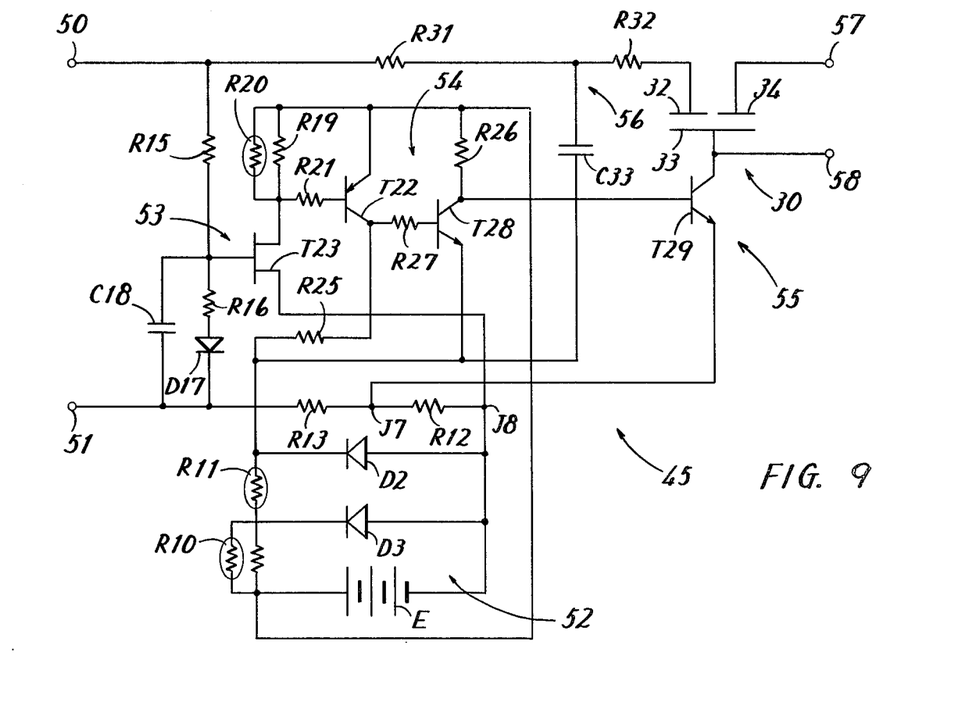
FIG. 9 is similar to FIG. 8 but shows a schematic diagram of the inventive electrolytic corrosion associated voltage integrating apparatus adapted to an earthed reference electrode made of zinc.

FIG. 9 is similar to FIG. 8 but shows a schematic diagram of another embodiment of the inventive electrolytic corrosion associated voltage integrating apparatus adapted to an earthed reference electrode made of zinc. As pointed out previously, an earthed reference electrode made of zinc comprises an earthed reference electrode-to-earth potential difference of −260 mV which is characteristic of the reference electrode material of zinc. In the FIG. 9 embodiment, therefore, it is necessary to reverse the polarity of the reference voltage source 52 as compared with that in the FIG. 8 embodiment. Thus, the circuit connection in connection with the battery E, Zener diodes D2 and D3, thermistors R11 and R10, and the resistors R13 and R12 is reversed with respect to the other portions in the circuit configuration. Other circuit connections are the same throughout both the FIGS. 8 and 9 embodiments, and therefore like portions are designated by the same reference characters.

Figure 10:
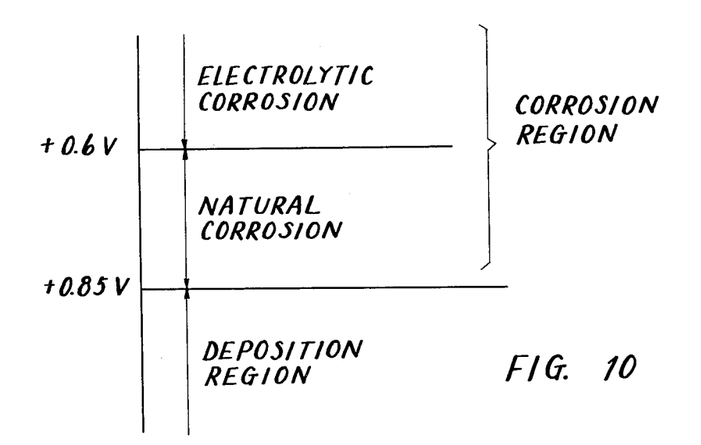
FIG. 10 shows a relation of corrosion voltage with various phenomena possible in an electric conductor subject to corrosion.

Now, it is appropriate to consider more fully corrosion of an electric conductor installed in contact with the earth. In general, such corrosion is classified as "natural corrosion" and "electrolytic corrosion" depending upon the causes of corrosion. Natural corrosion is caused by a chemical reaction by water, for example, while electrolytic corrosion is caused by a leakage current flowing from or to rails of electric railways. On the other hand, when corrosion measurement is made by a conductor-to-earthed reference electrode potential as in the case of the present invention, an earthed reference electrode comprises a particular potential difference with respect to the earth which is characteristic of the reference electrode material, as fully described in the foregoing. Therefore, assuming that an earthed reference electrode made of saturated cupric sulfate is employed, the polarity and the value of the conductor-to-reference electrode potential are classified as shown in FIG. 10. Referring to the FIG. 10 illustration, a region of the potential lower than the above-discussed potential difference of +850 mV characteristic of the saturated cupric sulfate electrode may be referred to as "corrosion region," while a potential region exceeding the above-mentioned potential difference of 850 mV may be referred to as "deposition region." Further, the above-mentioned corrosion region can be divided into "electrolytic corrosion region" and "natural corrosion region" with a certain value of threshold therebetween, say 600 mV, although such threshold value may be different depending upon the material of an electric conductor installed in contact with the earth because of difference in ionization tendency of such material.

In a certain application of corrosion measurement, it is desired to provide an indication predominantly associated with electrolytic corrosion. However, in another application of the corrosion measurement, it is desired to provide an indication associated with both electrolytic corrosion and natural corrosion. Therefore, it is preferred that the inventive apparatus be selectively adaptable to measurement of any types of corrosions occurring in any type of conductors using any type of earthed reference electrodes.

Figure 11:
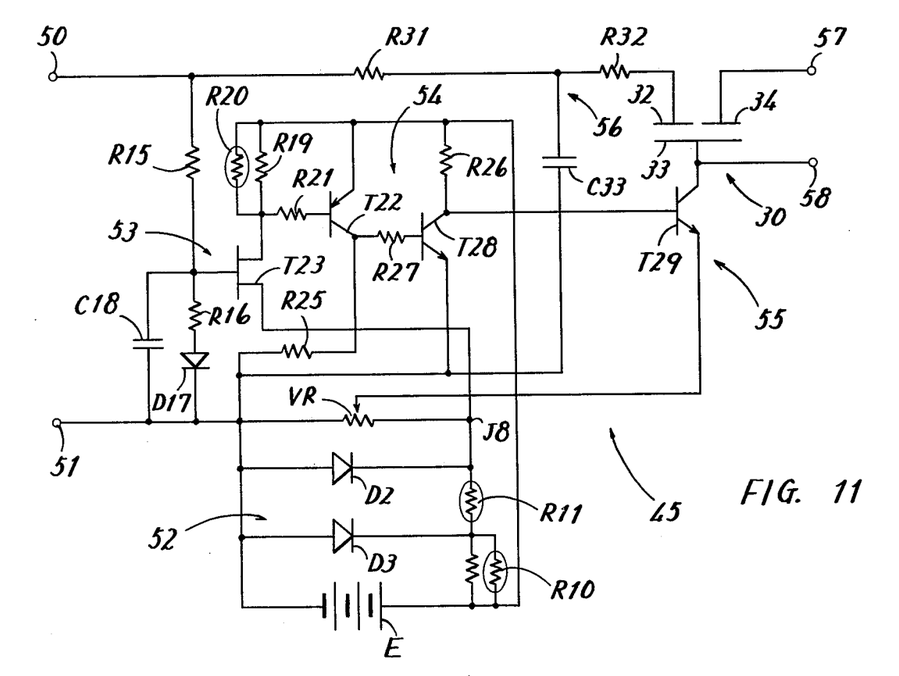
FIG. 11 shows a schematic diagram of a further embodiment of the inventive electrolytic corrosion associated voltage integrating apparatus adapted to provide versatile applications.

FIG. 11 shows a schematic diagram of a further embodiment of the inventive electrolytic corrosion measuring apparatus adapted to provide the above-mentioned versatility. The FIG. 11 embodiment is very similar to the FIG. 8 embodiment, but the resistors R13 and R12 in the FIG. 8 embodiment have been replaced by a variable resistor VR, while the other portions remain the same. Therefore, like portions are designated by the same reference characters. It is understood that proper adjustment of the variable resistor VR selects a desired threshold of corrosion regions discussed with reference to FIG. 10. As a result, an indication of the corrosion measurement by the present invention can be adjusted in advance depending upon the materials of conductors and the materials of the earthed reference electrodes for proper selection of corrosion regions and thus versatile application of the inventive apparatus can be expected.

As discussed with reference to FIG. 4, in a certain area of the conductor 43 of interest the leakage current flows from the conductor 43, while in another area of the conductor 43 the leakage current flows to the conductor 43, so that in the former situation electrolytic corrosion occurs and in the latter situation electrolytic deposition occurs. Nevertheless, such leakage current can vary from time to time in value and in polarity thereof and qualitative association of the conductor-to-earthed reference electrode potential with the amount of corrosion is also liable to vary. Therefore, separate measurement of the positive and negative going components of the conductor-to-earthed reference electrode potential is of much assistance in the consideration of the electrolytic corrosion of the electric conductor.

Figure 12:
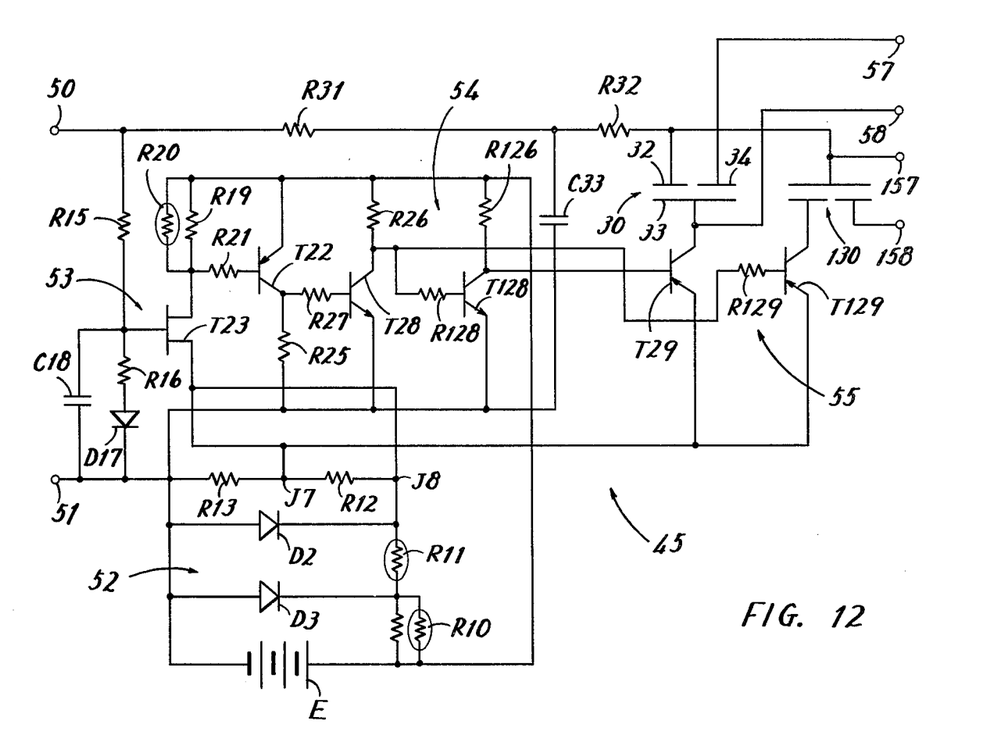
FIG. 12 is similar to FIG. 8 but shows a schematic diagram of still a further embodiment of the inventive electrolytic corrosion associated voltage integrating apparatus adapted to provide separate integration of positive and negative going components of the conductor-to-earthed reference electrode potential.

FIG. 12 is similar to FIG. 8 but shows a schematic diagram of still a further embodiment of the inventive electrolytic corrosion associated voltage integrating apparatus adapted to provide such separate measurement of the positive and negative going components of the conductor-to-earthed reference electrode potential. In comparing the FIG. 12 illustration with that in FIG. 8, another set of the potential memory device 130 and the switching transistor T129 are connected in parallel with the set of the potential memory device 30 and the switching transistor T29, such that the device 130 is reversed in polarity as compared with the device 30. For the purpose of driving the above-described two transistors T29 and T129 in an opposite polarity, an additional transistor T128 is provided in the DC amplifier 54, and the base of the transistor T29 is connected to the collector of the transistor T128, while the base of the transistor T129 is connected through a resistor R129 to the collector of the transistor T28. Although an additional stage of the transistor T128 was interposed in the DC amplifier 54, the transistor T29 was reversed to a PNP type as compared with that in FIG. 8, and, therefore, the transistor T29 is turned on only if and when the input conductor-to-reference electrode potential signal exceeds the above-described reference voltage. On the other hand, the base of the transistor T129, the conduction type of which is the same as that of transistor T29, is connected through the resistor R129 to the collector of the preceding transistor T28. Therefore, it is readily understood that the transistor T129 is turned on only if and when the conductor-to-reference electrode potential is less than the above-described reference voltage. As a result, the potential memory device 30 provides an integrated value of the positive going component of the conductor-to-reference electrode potential, while the potential memory device 130 provides an integrated value of the negative going component of the conductor-to-reference electrode potential.

Figure 13:
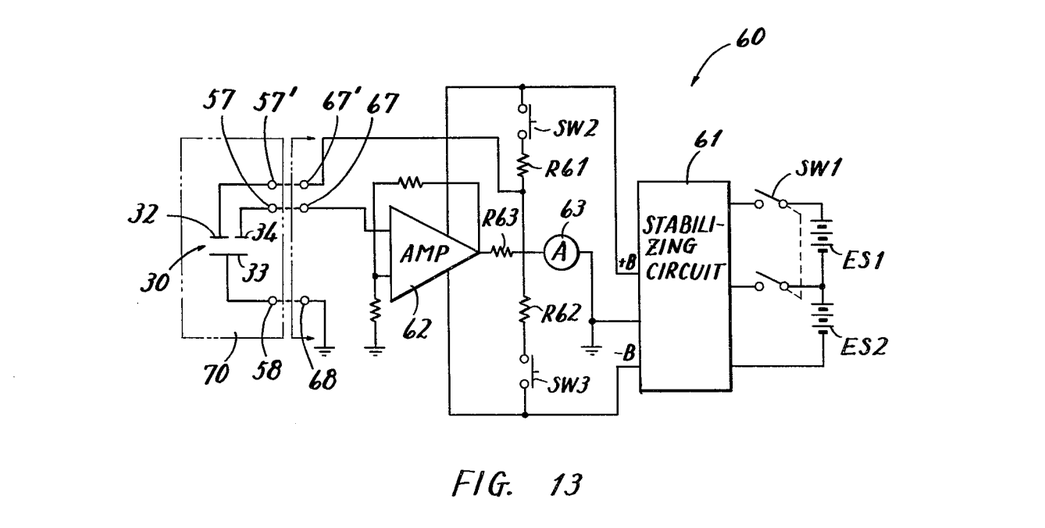
FIG. 13 shows a schematic diagram of a potential memory device module and a display circuit embodying the present invention.

In a preferred embodiment of the present invention, the above-described potential memory device 30 is detachably provided in the inventive electrolytic corrosion associated voltage integrating apparatus 45, preferably in a form of module. After corrosion measurement in the field using the inventive apparatus, the above-mentioned module comprising the potential memory device 30 is taken out of the apparatus 45 and the terminal voltage of the potential memory device 30 is measured using a display circuit. A schematic diagram of the above-described module and display circuit is shown in FIG. 13. Referring to FIG. 13, a module 70 comprises the above-described potential memory device 30 and output terminals 57', 57 and 58, connected to the main cathode 32, auxiliary cathode 34 and anode 33, respectively. On the other hand, the display circuit 60 comprises two sets of batteries ES1 and ES2 connected through a switch SW1 to a voltage stabilizing circuit 61, individual positive and negative stabilized output voltages +B and −B of which are fed to an amplifier 62 and also through a series connection of a switch SW2 and a resistor R61 and a series connection of a switch SW3 and a resistor R62, respectively, to a common terminal 67'. A voltmeter 63 is connected through a resistor R63 between an output of the said amplifier 62 and the ground. The display circuit 60 further comprises an input terminal 67 connected to an input to the amplifier 62 and a terminal 68 connected to the ground. The set of output terminals 57', 57 and 58 and the set of the input terminals 67', 67 and 68 are provided for mutual detachable connection.

In operation, the module 70 is taken out of the inventive electrolytic corrosion associated voltage integrating apparatus 45 and is brought back. Then, the module is connected to the display circuit 60. The power switch SW1 is turned on for energization of the circuit, so that the stabilized positive and negative output voltages +B and −B are supplied to the amplifier 62. Therefore, the terminal voltage between the auxiliary cathode 34 and the anode 33 is inputted to the amplifier 62 and an amplified output is displayed by means of the voltmeter 63.

After the above-mentioned indication by means of the voltmeter 63 is recorded, the switch SW2 is closed, so that a current flows from the positive output terminals +B through the switch SW2 and the resistor R61 to the main cathode 32 of the device, whereby the device 30 is discharged in terms of the present application to perform an initial setting of the device 30. In the event the device is discharged overly, then the switch SW3 is closed while the switch SW2 is opened, so that a current flows from a main cathode 32 of the device 30 through the terminals 57' and 67' and the resistor R62 and the switch SW3 to the negative output voltage terminal −B of the circuit 61, whereby the device is again charged. By proper operation of these switches SW2 and SW3, a desired initial setting of the device 30 is possible.

While the specific preferred embodiments of the invention have been described, it will be apparent that the obvious variations and modifications of the invention will occur to those of ordinary skill in the art from a consideration of the foregoing description. It is therefore desired that the present invention be limited only by the appended claims.

What is claimed is:

1. An apparatus for integrating a voltage associated with electrolytic corrosion which occurs in an electric conductor installed in electrical contact with the earth as a function of leakage current flowing therethrough, comprising:

an earthable reference electrode of given material adapted to be in good electrical contact with the earth, said earthable reference electrode having a characteristic potential difference, between said earthable reference electrode and the earth per se, which is characteristic of said given material of said electrode, potential memory device means having at least one cathode and an anode and responsive to an input voltage across said anode and said at least one cathode for storing an electrical charge indicative of said input voltage, and for exhibiting, between said anode and said at least one cathode, a terminal voltage which is linearly changeable in direct proportion to the electrical charge stored therein, comparing means adapted to be connected to said electrical conductor and said earthable reference electrode for detecting a potential difference between said electric conductor and said earthable reference electrode, said potential difference representing said voltage associated with electrolytic corrosion, reference voltage means for providing a reference voltage selected for compensation of said potential difference between said earthable reference electrode and the earth per se, said comparing means providing a comparison output only when said potential difference between said electric conductor and said earthable reference electrode differs from said reference voltage, switching means operatively associated with said comparing means and said potential memory device means for controlling said potential memory device means, output means connected to said anode and said at least one cathode of the device for providing an indication of an integrated value of said voltage associated with electrolytic corrosion occurring in said electric conductor in terms of said terminal voltage of said potential memory device means, and said switching means being responsive to said comparison output of said comparing means for controlling said potential memory device means to conduct so as to vary the electrical charge stored therein, whereby said output of said output means is compensated for the characteristic potential difference between said earthable reference electrode and the earth per se.

2. The electrolytic corrosion associated voltage integrating apparatus in accordance with claim 1, in which said apparatus further comprises
means for adjusting said reference voltage of said reference voltage means.

3. The electrolytic corrosion associated voltage integrating apparatus in accordance with claim 1, which further comprises means for choosing one polarity component of said voltage associated with electrolytic corrosion for applying to said memory device means.

4. The electrolytic corrosion associated voltage integrating apparatus in accordance with claim 3, in which there is further provided a second means for choosing the opposite polarity component of said voltage associated with electrolytic corrosion, and
said potential memory device means comprises
a first potential memory device connected to said first means for choosing one polarity component of said voltage, and
a second potential memory device connected to said second means for choosing the opposite polarity component of said voltage.

5. The electrolytic corrosion associated voltage integrating apparatus in accordance with claim 3, in which said means for choosing one polarity component of said voltage comprises unidirectional conductor means.

6. The electrolytic corrosion associated voltage integrating apparatus in accordance with claim 3, in which said means for choosing one polarity component of said leakage current comprises
   means for judging polarity of the leakage current, and
   means responsive to said polarity judging means for selectively switching an input to said potential memory device means.

7. The electrolytic corrosion associated voltage integrating apparatus in accordance with claim 1, in which said at least one cathode comprises
   a main cathode including an active metal connected to receive said electrolytic corrosion associated voltage, and
   an auxiliary cathode including an active metal connected to said output means for providing said integrated value of said electrolytic corrosion associated voltage.

8. The electrolytic corrosion associated voltage integrating apparatus in accordance with claim 1, which further comprises
   means for selectively and forcibly charging or discharging said potential memory device means for initial adjustment of the potential memory device means.

9. The electrolytic corrosion associated voltage integrating apparatus in accordance with claim 1, in which said output means comprises
   means for amplifying a terminal voltage of the memory device, and
   means for indicating an output of said amplifying means.

10. The electrolytic corrosion associated voltage integrating apparatus in accordance with claim 1, which further comprises means for detachably connecting said potential memory device means to the preceding and succeeding stage of the apparatus.

11. The electrolytic corrosion associated voltage integrating apparatus in accordance with claim 1, which further comprises means for detachably connecting said output means to said potential memory device means.

12. An apparatus for integrating a voltage associated with electrolytic corrosion which occurs in an electric conductor installed in electrical contact with the earth as a function of leakage current flowing therethrough, said apparatus comprising in combination:
   an earthable reference electrode of given material adapted to be in good electrical contact with the earth, said earthable reference electrode having a characteristic potential difference, between said earthable reference electrode and the earth per se, which is characteristic of said given material of said electrode,
   potential memory device means having at least one cathode and anode, each adapted to be connected to a respective one of said electric conductor and said earthable reference electrode and responsive to a conductor-to-earthable reference electrode potential difference therebetween for storing an electrical change indicative of said conductor-to-earthable reference electrode potential difference, and for exhibiting, between said anode and said at least one cathode, a terminal voltage output which is linearly changeable in direct proportion to the electrical charge stored therein, and
   comparing means operatively associated with said potential memory device means, and connected to said electric conductor and said earthable reference electrode, for detecting when said conductor-to-earthable reference electrode potential difference is of a first polarity with respect to a zero voltage, whereby to permit storing of said electrical charge by said potential memory device means, and for detecting when said conductor-to-earthable reference electrode potential difference is of a second polarity opposite to said first polarity with respect to said zero voltage, whereby to inhibit said storing of said electrical charge by said potential memory device means,
   said apparatus further including reference voltage means operatively associated with said comparing means for imposing on said comparing means a reference voltage so as to adjust said zero voltage for detecting said first and second polarities, whereby to compensate said terminal voltage output of said potential memory device means for the harmful effect of said earthable reference electrode-to-earth potential difference on said integrating of said voltage associated with said electrolytic corrosion.

13. The apparatus of claim 12 wherein said reference voltage means includes means for adjusting said reference voltage imposed on said comparing means.

14. The apparatus of claim 12 wherein said conductor-to-earthable reference electrode includes a low frequency corrosion current component and a high frequency transmission-induced component superimposed thereon, said apparatus including filter means operatively associated therewith for filtering out said high frequency transmission-induced component.

15. The apparatus of claim 14 wherein said filter means is connected between said earthable reference electrode and said potential memory device means.

16. The apparatus of claim 14 wherein said filter means is connected between said conductor and said comparing means.

17. A system for displaying the integration of a voltage associated with electrolytic corrosion, said system comprising an apparatus as set forth in claim 12, the system further comprising display means connected to said cathode of said potential memory device means for displaying said terminal difference between said anode and said at least one cathode of said potential memory device means, whereby to provide a display of the integrated value of said voltage associated with said electrolytic corrosion.

* * * * *

UNITED STATES PATENT AND TRADEMARK OFFICE
CERTIFICATE OF CORRECTION

PATENT NO. : 4,209,376
DATED : June 24, 1980
INVENTOR(S) : Yoichi Arita et al.

It is certified that error appears in the above-identified patent and that said Letters Patent are hereby corrected as shown below:

Column 2, line 7, "al" should be --al.--;
Column 2, line 14, "Apr." should be --April--.
Column 3, line 8, after "voltage" delete --,--.
Column 7, line 63, after "cutting" delete --off--.
Column 9, line 33, "comparison" should be --compare--;
Column 9, line 45, "comparison" should be --compare--;
Column 9, line 50, "comparison" should be --compare--;
Column 9, line 51, "comparison" should be --compare--;
Column 9, line 63, "comparison" should be --compare--;
Column 9, line 65, "comparison" should be --compare--.

Signed and Sealed this

Tenth Day of February 1981

[SEAL]

Attest:

RENE D. TEGTMEYER

Attesting Officer

Acting Commissioner of Patents and Trademarks